US00PP28886P2

(12) United States Plant Patent
Hesselein

(10) Patent No.: US PP28,886 P2
(45) Date of Patent: Jan. 23, 2018

(54) ***CALYCANTHUS* PLANT NAMED 'BURGUNDY SPICE'**

(50) Latin Name: *Calycanthus floridus*
Varietal Denomination: Burgundy Spice

(71) Applicant: Richard L. Hesselein, Allentown, NJ (US)

(72) Inventor: Richard L. Hesselein, Allentown, NJ (US)

( * ) Notice: Subject to any disclaimer, the term of this patent is extended or adjusted under 35 U.S.C. 154(b) by 0 days.

(21) Appl. No.: 15/530,254

(22) Filed: Dec. 15, 2016

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

(56) References Cited

PUBLICATIONS http://www.nurserymag.com/article/color-is-king/; Mar. 31, 2016; 18 pages.*

* cited by examiner

*Primary Examiner* — Kent L Bell
(74) *Attorney, Agent, or Firm* — Audrey Charles

(57) ABSTRACT

A new and distinct cultivar of *Calycanthus* plant named 'Burgundy Spice', characterized by its reddish-maroon colored flowers, dark greyish-purple colored foliage, and moderately vigorous, upright growth habit, is disclosed.

1 Drawing Sheet

Latin name of genus and species of plant claimed: *Calycanthus floridus.*

Variety denomination: 'Burgundy Spice'.

BACKGROUND OF THE INVENTION

The present invention relates to a new and distinct cultivar of *Calycanthus* plant botanically known as *Calycanthus floridus* and hereinafter referred to by the cultivar name 'Burgundy Spice'.

The new cultivar originated in a controlled breeding program during August 2011 in Allentown, N.J. The objective of the breeding program was the development of *Calycanthus* cultivars having large leaves and dark colored foliage.

The new *Calycanthus* cultivar is a naturally-occurring sport of a proprietary breeding selection, not coded, not patented, characterized by its dark green to purple colored foliage. The new cultivar was discovered as a side shoot and selected during August 2011 in a controlled environment in Allentown, N.J.

Asexual reproduction of the new cultivar by terminal stem cuttings since August 2011 in Allentown, N.J. has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Burgundy Spice' as a new and distinct cultivar of *Calycanthus* plant:

1. Reddish-maroon colored flowers;
2. Dark greyish-purple colored foliage; and
3. Moderately vigorous, upright growth habit.

Plants of the new cultivar differ from plants of the female parent primarily in having foliage that is dark greyish-purple and stable in coloration.

Of the many commercially available *Calycanthus* cultivars, the most similar in comparison to the new cultivar is 'Athens', not patented. However, in comparison, plants of the new cultivar differ from plants of 'Athens' in at least the following characteristics:

1. Plants of the new cultivar have a foliage color that is different from plants of 'Athens'; and
2. Plants of the new cultivar have a tepal color that is different from plants of 'Athens'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Burgundy Spice'. The plants were approximately two-years old and grown for 10 months in the landscape in West Grove, Pa.

DETAILED BOTANICAL DESCRIPTION

Figure 1:
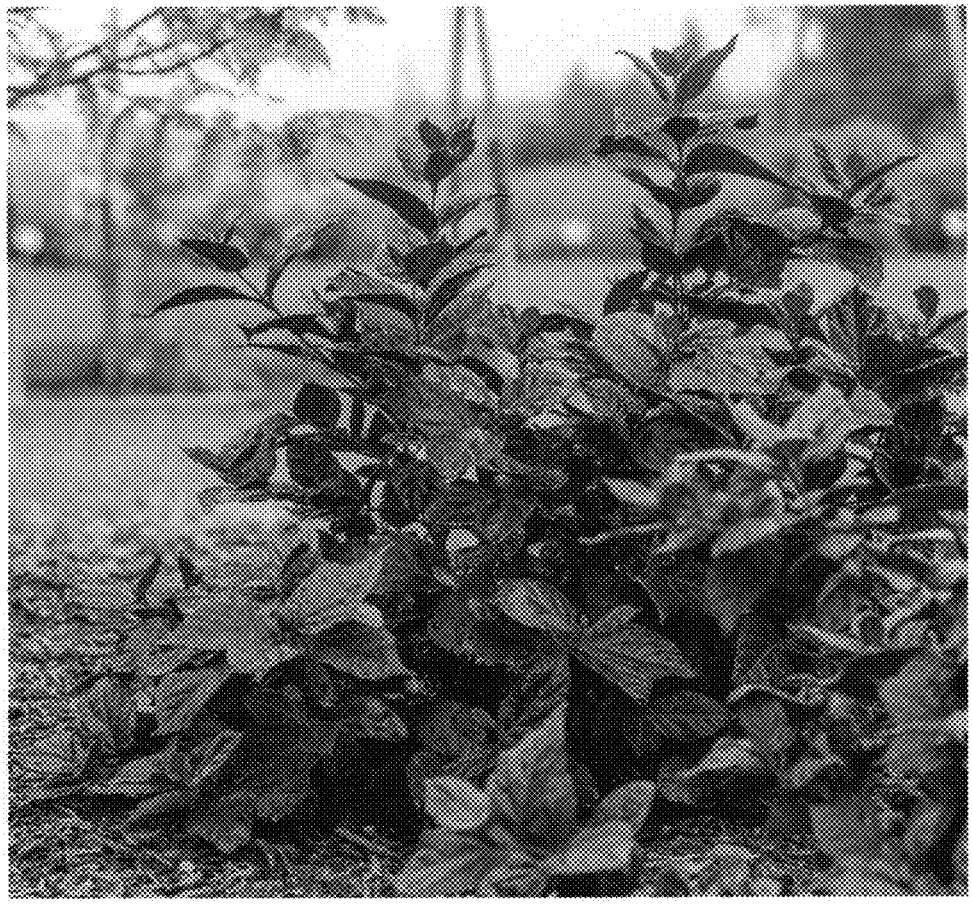
FIG. 1 illustrates a side view of the overall growth and flowering habit of 'Burgundy Spice'.
Figure 2:
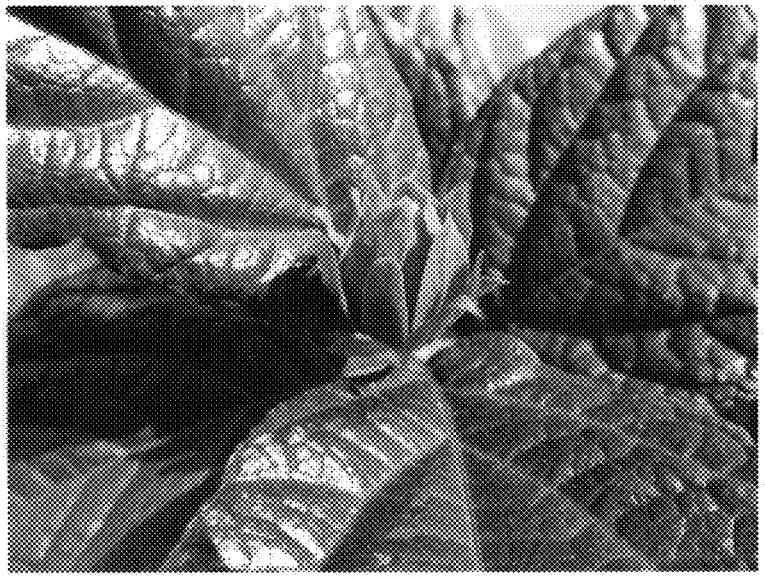
FIG. 2 illustrates a close-up view of an individual inflorescence of 'Burgundy Spice'

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2016 under natural light conditions in West Grove, Pa.

The following descriptions and measurements describe 2-year old plants produced from cuttings from stock plants and grown outside in a landscape trial setting for 10 months in West Grove, Pa. During the outdoor growth period the daily maximum temperatures ranged from 89° F. to 14° F. (31.7° C. to −10° C.) and the daily minimum temperatures ranged from 73° F. to 5° F. (22.8° C. to −15° C.). Measurements and numerical values represent averages of typical plants.

Botanical classification: *Calycanthus floridus* cultivar Burgundy Spice.

Parentage:

*Parent*.—Proprietary breeding selection, not coded, not patented.

Propagation:

*Type cutting*.—Softwood.

*Time to initiate roots*.—Approximately 28 to 42 days.

*Time to produce a rooted cutting*.—Approximately 70 to 84 days.

*Root description*.—Fine to thick; white to brown in color.

*Rooting habit*.—Freely branching; dense.

Plant description:

*Commercial crop time*.—Approximately 52 to 54 weeks from a rooted cutting to finish in a 11.35 liter pot.

*Growth habit and general appearance*.—Multi-stemmed deciduous shrub, moderately vigorous, upright growth habit.

*Hardiness*.—USDA Zone 6b (−5° F.).

*Size*.—Height from soil level to top of plant plane: Approximately 55.0 cm. Width: Approximately 50.0 cm.

*Branching habit*.—Freely branching. Pinching enhances branching. Quantity of lateral branches per plant: Approximately 10.

*Trunk*.—Diameter at soil level: Approximately 1.5 cm. Diameter at midpoint: Approximately 6.0 mm. Texture: Glabrous to scabrid. Color: N200B.

*Branch*.—Shape: Rounded. Strength: Strong. Arrangement: Opposite. Aspect: Erect to about 45° from main stem. Length to base of inflorescence: Approximately 9.0 cm. Diameter: Approximately 2.0 mm. Length of central internode: Approximately 3.8 cm. Texture of young stem: Glabrous to tomentulose. Texture of mature stem: Woody. Color of young stem: 177A. Color of mature stem: N200B.

Foliage description:

*General description*.—Form: Simple. Arrangement: Opposite. Fragrance: None detected.

*Leaves*.—Shape: Elliptic. Margin: Entire. Apex: Attenuate. Base: Obtuse. Venation pattern: Pinnate. Length of mature leaf: Approximately 7.8 cm. Width of mature leaf: Approximately 4.5 cm. Texture of upper and lower surfaces: Glabrous to tomentulose. Color of upper surface of young and mature foliage: Closest to N92A with venation of 144A or 172B in full sun. Color of lower surface of young and mature foliage: Closest to N77 with venation of 59A.

*Petiole*.—Length: Approximately 1.5 cm. Diameter: Approximately 3.0 mm. Texture: Glabrous to tomentulose. Color: 197A.

Flowering description:

*Flowering season*.—Flowers in late spring and sporadically through mid-summer.

*Lastingness of individual inflorescence on the plant*.—Approximately 15 to 20 days.

Flower description:

*General description*.—Type: Single, flowers on current season's growth, terminal and often on subtending axils; tepals arranged in a whorl. Quantity per plant: Approximately 12 flowers open at a given time. Fragrance: Strongly fragrant; melon-like. Aspect: Erect.

*Bud just before opening*.—Shape: Globose. Length: Approximately 1.0 cm. Diameter: Approximately 1.0 cm. Color: 187A.

*Perianth*.—Shape: Magnolia-like. Depth: Approximately 2.5 cm. Diameter: Approximately 3.5 cm.

*Tepals/bracts*.—Quantity: Approximately 34. Shape: Linear. Margin: Entire. Apex: Acute. Base: Truncate. Length: Approximately 1.5 cm. Width: Approximately 4.0 mm. Texture of upper and lower surfaces: Glabrous. Color of upper and lower surfaces: 183A.

*Peduncle*.—Strength: Strong. Aspect: Erect. Length: Approximately 1.0 cm. Diameter: Approximately 3.0 mm. Texture: Tomentulose. Color: N144C.

*Reproductive organs*.—Androecium: Stamen quantity per flower: 19. Anther shape: Oblong, adnate to hypanthium. Anther length: Approximately 3.0 mm. Anther color: 161A. Pollen amount: Moderate. Pollen color: 4C. Gynoecium: Pistil quantity per flower: 1. Pistil length: Approximately 3.0 mm. Stigma shape: Rounded. Stigma color: 142C. Style length: Approximately 2.0 mm. Style color: 142C. Ovary length: Approximately 1.0 mm. Ovary color: 142B.

*Fruit*.—Diameter: Approximately 1.0 cm. Width: Approximately 1.5 cm. Color: 138A. Texture: Sparsely pubescence.

Seed production: Seed production has not been observed.

Disease and pest resistance: Resistance to pathogens and pests common to *Calycanthus* has not been observed.

What is claimed is:

1. A new and distinct cultivar of *Calycanthus* plant named 'Burgundy Spice', substantially as herein illustrated and described.

* * * * *